United States Patent [19]

Crochemore

[11] Patent Number: 5,777,151
[45] Date of Patent: Jul. 7, 1998

[54] ESTERIFICATION OF CARBOXYLIC ACID SALTS

[75] Inventor: Michel Crochemore, Chaponost, France

[73] Assignee: Rhone-Poulenc Chimie, Courbevoie Cedex, France

[21] Appl. No.: 950,233

[22] Filed: Sep. 24, 1992

[30] Foreign Application Priority Data

Sep. 24, 1991 [FR] France ................................ 91 11747

[51] Int. Cl.⁶ .......................... C07C 69/76; C07C 69/00
[52] U.S. Cl. .............................................................. 560/61
[58] Field of Search ................................ 560/143, 75, 61

[56] References Cited

U.S. PATENT DOCUMENTS 4,334,079  6/1982  Greene et al. ............................ 560/75

FOREIGN PATENT DOCUMENTS

A-2331545  6/1977  France.
A-916772   1/1963  United Kingdom.

OTHER PUBLICATIONS

Nobatov et al. "Preparation of complex esters of 2-(4-hydroxyphenoxy) propionic acid under phase-transfer catalysis", Chemical Abstract vol 111 No. 57190, abstract, 1989.

Chemical Abstract vol. 103, No. 22250d, Barry et al. 1985 "Solid–liquid phase–transfer catalysis".

"Solid Liquid Phase-Transfer Catalysis without Added Solvent. A Simple, Efficient, and Inexpensive Synthesis of Aromatic Carboxylic Esters by Alkylation of Potassium Carboxylates", Synthesis, 1985, No. 1 Jan., pp. 40–45.

Primary Examiner—C. Warren Ivy
Assistant Examiner—Raymond Covington
Attorney, Agent, or Firm—Burns, Doane, Swecker & Mathis, L.L.P.

[57] ABSTRACT

Mono- or polycarboxylic acid esters are prepared by reacting a salt of such carboxylic acid with an organic halocompound, e.g., a (cyclo)alkyl, (cyclo)alkenyl, aryl or aralkyl halide, in an aqueous reaction medium, in the presence of a catalytically effective amount of a phase transfer catalyst, for example an onium salt.

34 Claims, No Drawings

ESTERIFICATION OF CARBOXYLIC ACID SALTS

BACKGROUND OF THE INVENTION

1. Field of the Invention

The present invention relates to the esterification of salts of carboxylic acids, and more especially, to the esterification of the salts of both monocarboxylic and polycarboxylic acids.

2. Description of the Prior Art

U.S. Pat. No. 3,341,575 describes the preparation of esters from alkyl halides and salts of carboxylic acids, in an amide-type solvent, particularly dimethylformamide, in the presence of an iodine compound.

FR-A-1,294,105 describes preparing the alkyl esters of carboxylic acids by reacting a carboxylic acid with equimolecular amounts of an alkyl halide and a tertiary aliphatic amine. Exemplary such esters of the following acids or anhydrides have been prepared by this process: phthalic, caproic and adipic acid, succinic anhydride, maleic anhydride, phthalic anhydride, acid n-butyl phthalate, 4-ethyl mercapto-alpha-hydroxybutyric acid, and the like.

The various methods described entail the use of solvents and result in polluting, inefficient operations.

Furthermore, esterification of carboxylic acids displaying steric hindrance at the alpha position or otherwise at the locale of the carboxyl function presents difficulties, and slow reaction speeds are often the rule.

SUMMARY OF THE INVENTION

Accordingly, a major object of the present invention is the provision of an improved technique for the esterification of salts of the carboxylic acids which avoids, or conspicuously ameliorates, the above disadvantages and drawbacks to date characterizing the state of this art.

Briefly, the present invention features esterifying a salt of a carboxylic acid, comprising reacting a salt of a carboxylic acid with a halogenated derivative of an aliphatic hydrocarbon, a cycloaliphatic hydrocarbon or an aliphatic hydrocarbon bearing a cyclic substituent in an aqueous medium, in the presence of a phase transfer catalyst.

DETAILED DESCRIPTION OF THE PREFERRED EMBODIMENTS OF THE INVENTION

More particularly according to the present invention, the salt of the carboxylic acid and the halogenated derivative, or organic halocompound, are reacted in an aqueous medium, in the absence of any organic solvent.

Indeed, it has now unexpectedly been found that the process of the invention permits esters of carboxylic acids, particularly benzoic acids, to be prepared in an aqueous medium in excellent yields. This result is completely surprising, since one skilled in this art would have expected the halocompound to be hydrolyzed which would reduce the yield of the reaction.

By the generic term "halogenated derivative" or "halocompound" are intended the halogenated compounds indicated above.

By the expression "phase transfer catalyst" is intended a catalyst which transfers the carboxylate anion from the aqueous phase into the organic phase.

The process of the present invention is applicable to any salt derived from a mono- or polycarboxylic acid, such as saturated or unsaturated aliphatic carboxylic acids; monocyclic or polycyclic, saturated, unsaturated or aromatic carbocyclic or heterocyclic carboxylic acids; or saturated or unsaturated aliphatic carboxylic acids being a cyclic substituent, such as a saturated, unsaturated or aromatic carbocyclic or heterocyclic ring member.

The subject process is very well adapted for the preparation of esters of aromatic carboxylic acids, particularly benzoic acids, especially those exhibiting steric hindrance in the vicinity of the carboxyl group.

In the following description of the invention, by the term "aromatic compound" is intended the classical definition of aromaticity as reported in the literature, particularly by Jerry March, *Advanced Organic Chemistry*, 3rd Edition, pp. 37 ff, John Wiley & sons (1985).

By "benzoic acid" is intended any aromatic compound bearing at least one —COOH group.

Characteristically, such carboxylic acid salt has the formula (I):

$$[Q-COO^-]_w M^{w+} \qquad (I)$$

in which Q is an optionally substituted hydrocarbon radical having from 1 to 40 carbon atoms; M is a metal carboxylate group; and w represents the valency of the metal M.

The carboxylic acid salts are preferably of formula (I), wherein Q is a hydrocarbon radical, optionally substituted, having from 1 to 20 carbon atoms and M is a metal cation of Group Ia or IIa of the Periodic Table, or an ammonium radical.

Any carboxylic acid salt may be employed in the reaction according to the invention, provided that it is soluble enough in water to permit the process to be carried out easily.

From a practical and economic point of view, the metal salts of Group IA are used, namely, alkali metals, preferably sodium and potassium, as well as the metal salts of Group IIA, i.e., alkaline earth metals and more particularly magnesium, calcium or barium; or ammonium salts.

In formula (I), w is preferably equal to 1 or 2.

According to the invention, the starting material used is a carboxylic acid salt of formula (I), wherein the radical Q is a substituted or unsubstituted hydrocarbon radical which may be a straight or branched, saturated or unsaturated acyclic aliphatic radical; or a monocyclic or polycyclic, saturated, unsaturated or aromatic, carbocyclic or heterocyclic radical.

The carboxylic acid salts of general formula (I), wherein Q is a monocyclic or polycyclic, aromatic hydrocarbon radical, are particularly suitable for carrying out the process of the invention.

Preferably, Q is an aromatic hydrocarbon radical, particularly a benzene radical of the following general formula (II):

wherein n is an integer ranging from 0 to 5, preferably 0 to 3; R is $R_1$, namely, a straight or branched alkyl radical having from 1 to 6, preferably 1 to 4 carbon atoms, such as methyl, ethyl, propyl, isopropyl, butyl, isobutyl, sec-butyl or tert-butyl radical, a straight or branched alkenyl radical having from 2 to 6, preferably 2 to 4 carbon atoms, such as a vinyl or allyl radical, a straight or branched alkoxy radical having from 1 to 6, preferably 1 to 4 carbon atoms, such as the methoxy, ethoxy, propoxy, isopropoxy and butoxy radicals, a radical of the formulae —$R_2$—OH, —$R_2$—COOM, —$R_2$—CHO, —$R_2$—$NO_2$, —$R_2$—CN, —$R_2$—$NH_2$, —$R_2$—SH, —$R_2$—X, —$R_2$—$CF_3$, in which $R_2$ is a simple valence bond or a saturated or unsaturated, straight or branched, divalent hydrocarbon radical having from 1 to 4 carbon atoms, such as a methylene, ethylene, propylene, isopropylene or isopropylidene radical; X is a halogen atom, preferably a chlorine, bromine or fluorine atom and M is as defined above; or R is $R_3$, namely, a radical

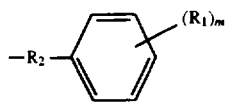

wherein $R_1$ and $R_2$ are as defined above and m is an integer ranging from 0 to 3, or a radical —$R_2$—A—$R_4$ in which $R_2$ is as defined above, and $R_4$ is a straight or branched alkyl radical having from 1 to 6, preferably 1 to 4 carbon atoms, or a radical of the formula:

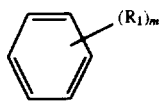

and A is one of the following groups:

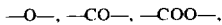

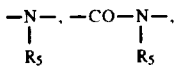

in which $R_5$ is a hydrogen atom or a straight or branched alkyl radical having from 1 to 4 carbon atoms, preferably a methyl or ethyl radical.

When n is greater than 1, the radicals R may be identical or different and two successive carbon atoms in the benzene ring may be interconnected by a ketal bridge, such as the extranuclear methylene dioxy or ethylene dioxy radicals.

It is preferable for n to be equal to 0, 1, 2 or 3.

From among the Q radicals indicated above, those which are the preferred are the carboxylic acid salts of general formula (I), wherein Q is an aromatic radical of general formula (II), in which n is 0, 1, 2 or 3; and R is a hydrogen atom, a straight or branched alkyl radical having from 1 to 4 carbon atoms, a straight or branched alkoxy radical having from 1 to 4 carbon atoms, a methylene or ethylene dioxy radical, an —OH group, a —CHO group, a phenyl or benzyl radical, or a halogen atom.

It is even more preferable to select compounds of formula (I) in which the radicals R, which may be the same or different, are each a hydrogen atom, a hydroxyl group, a methyl radical, a methoxy radical or a —CHO group.

Q may also be a polycyclic aromatic hydrocarbon radical, wherein the ring members may together form ortho- condensed or ortho- and pericondensed systems. A naphthalene radical is particularly representative, in which the ring members may be substituted by 1 to 4, preferably 1 to 3, radicals $R_1$, in which $R_1$ is as defined above for substituents of the aromatic hydrocarbon radical of general formula (II).

In general formula (I) for the carboxylic acid salts, Q may also be a carbocyclic radical which is saturated or which has 1 or 2 sites of unsaturation in the ring, and which generally has 3 to 7 and preferably 6 carbon atoms in the ring. The ring may be substituted by 1 to 5 radicals $R_1$, preferably 1 to 3, in which $R_1$ is as defined above for substituents of the aromatic hydrocarbon radical of general formula (II).

Exemplary preferred Q radicals are cyclohexyl and cyclohexenyl optionally substituted by straight or branched alkyl radicals having from 1 to 4 carbon atoms.

As indicated above, Q may be a straight or branched, saturated or unsaturated, acyclic aliphatic radical.

More specifically, Q may be a straight or branched, acyclic aliphatic hydrocarbon radical, preferably having 1 to 12 carbon atoms, which may be saturated or have one or more sites of unsaturation along its backbone, generally 1 to 3 sites of unsaturation which may be single or conjugate double bonds or triple bonds. Such hydrocarbon chain may optionally be interrupted by one of the following groups:

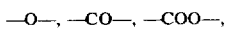

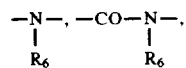

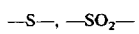

wherein $R_6$ is a hydrogen atom or a straight or branched alkyl radical having from 1 to 4 carbon atoms, preferably a methyl or ethyl radical, and/or bear one of the following substituents:

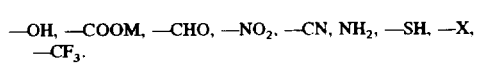

The straight or branched, saturated or unsaturated, acyclic aliphatic radical may optionally bear a cyclic substituent. By the term "cyclic substituent" is intended a saturated, unsaturated or aromatic, carbocyclic or heterocyclic ring member The acyclic aliphatic radical may be bonded to the ring via a simple valence bond or via one of the following groups:

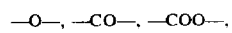

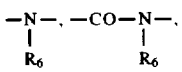

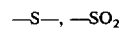

in which $R_6$ is as defined above.

Exemplary such cyclic substituents include aromatic o heterocyclic, cycloaliphatic substituents, particularly cycloaliphatic radicals having 6 carbon atoms in the ring o benzene radicals, the cyclic substituents themselves option ally bearing 1, 2, 3, 4 or 5 identical or different radicals $R_1$ in which $R_1$ is as defined above for substituents of th aromatic hydrocarbon radical of general formula (II).

In the general formula (I) of the carboxylic acid salts, ( may also be a saturated or unsaturated heterocyclic radical particularly having 5 or 6 atoms in the ring, including 1 o 2 heteroatoms such as nitrogen, sulfur and oxygen atoms Some or all of the carbon atoms in the heterocycle ma optionally be substituted by radicals $R_1$, in which $R_1$ is a defined above for substituents of the aromatic hydrocarbo radical of general formula (II).

Q too may be a polycyclic heterocyclic radical, defined a being either a radical comprising at least two aromatic o non-aromatic heterocycles, containing at least one heteroa tom in each ring and together forming orthocondensed or ortho- and pericondensed systems, or alternatively a radical comprising at least one aromatic or non-aromatic hydrocarbon ring and at least one aromatic or non-aromatic heterocycle, together forming orthocondensed or ortho- and pericondensed systems. Some or all of the carbon atoms in these rings may optionally be substituted by radicals $R_1$, in which $R_1$ is as defined above for substituents of the aromatic hydrocarbon radical of general formula (II).

The carboxylic acid salts including at least one carboxylic group of formula (I) more particularly include the salts derived from the following carboxylic acids:

(i) saturated aliphatic monocarboxylic acids such as formic, acetic, propionic, butyric, isobutyric, valeric, isovaleric, pivalic, lauric, myristic, palmitric and stearic.

(ii) saturated aliphatic dicarboxylic acids, such as oxalic, malonic, succinic, glutaric, adipic, pimelic, suberic, azelaic or sebacic, (iii) unsaturated aliphatic monocarboxylic or dicarboxylic acids such as acrylic, propiolic, methacrylic, crotonic, isocrotonic, oleic, maleic, fumaric, citraconic or mesaconic, (iv) saturated or unsaturated carbocyclic carboxylic acids such as camphoric or chrysanthemic acid, (v) heterocyclic carboxylic acids such as furancarboxylic, thiophenecarboxylic, pyrrolcarboxylic, pyrazinecarboxylic, nicotinic, isonicotinic or picolinic acid, (vi) aromatic carbocyclic carboxylic acids such as benzoic, phthalic, isophthalic, terephthalic, naphthalenecarboxylic or toluic acids, (vii) saturated arylaliphatic carboxylic acids, particularly such as arylpropionic acids, e.g., 2-phenylpropionic acid, 2-|4(2-butyl)phenyl|propionic acid, 2-(3-benzoylphenyl)propionic acid, 2-(6-methoxy-2-naphthyl)propionic acid or unsaturated acids such as 2-phenylpropenoic acid or cinnamic acid, (viii) halogenated carboxylic acids such as monochloroacetic, dichloroacetic, trichloroacetic, monochloropropionic, α-bromopropionic, α-bromobutyric or trifluoroacetic acid, (ix) aliphatic, cycloaliphatic or arylaliphatic hydroxy acids, such as glycolic, lactic, glyceric, 2-hydroxybutanoic, 3-hydroxybutanoic, 2-methyllactic, 2-hydroxy-4-methylthiobutanoic, tartronic, malic, tartaric, 1-hydroxy cyclopropane carboxylic, 2-hydroxyphenylpropanoic, 2-hydroxycinnamic, 3-hydroxycinnamic or 4-hydroxycinnamic acid.

(x) the following hydroxybenzoic acids: 2-hydroxybenzoic (salicylic acid), 3-hydroxybenzoic, 4-hydroxybenzoic, 3-methylsalicylic, 4-methylsalicylic, 5-methylsalicylic, 3-hydroxy-4-methylbenzoic, 3-methoxysalicylic, 4-methoxysalicylic, 5-methoxysalicylic, 3-hydroxy-4-methoxybenzoic (isovanillic acid), 4-hydroxy-3-methoxybenzoic (vanillic acid), 3-hydroxy-4,5-dimethoxybenzoic, 4-hydroxy-3-dimethoxybenzoic (syringic acid), 5-hydroxyisophthalic, 3-aminosalicylic, 4-aminosalicylic, 5-aminosalicylic, 3-hydroxy-2-aminobenzoic, 3-nitrosalicylic, 3-hydroxy-4-nitrobenzoic, 4-hydroxy-3-nitrobenzoic, 3-hydroxy-4-methyl-2-nitrobenzoic, 3,5-diiodosalicylic, 2,3-dihydroxybenzoic, 2,4-dihydroxybenzoic, 2,5-dihydroxybenzoic, 2,6-dihydroxybenzoic, 3,4-dihydroxybenzoic, (protocatechuic acid), 3,5-dihydroxybenzoic, 3,5-dihydroxy-4-methylbenzoic, 2,3,4-trihydroxybenzoic, 2,4,6-trihydroxybenzoic or 3,4,5-trihydroxybenzoic acid.

(xi) alkoxy and phenoxy acids such as methoxyacetic, phenoxyacetic, 2,4-dichlorophenoxyacetic, phenoxypropionic, 2,4-dichlorophenoxypropionic, p-hydroxyphenoxypropionic, m-chlorophenoxypropionic, 4-phenoxybenzoic acid, (4-carboxy-4-phenoxy)benzoic acid or piperonylic acid.

(vii) oxo acids such as 2-acetylbenzoic, 4-acetylbenzoic, 2-benzoylbenzoic or 4-benzoylbenzoic, (viii) acyloxy acids such as 3-benzoyloxypropionic, 2-acetoxybenzoic or 4-acetoxybenzoic acid, (xiv) amido acids such as 2-acetamidoacrylic, 2-acetamidobenzoic, 3-acetamidobenzoic or 4-N-acetamidobenzoic acid, (xv) amino acids which are N-protected by a protective group such as the following: acyl (acetyl, benzoyl), BOC (butyloxycarbonyl), CBZ (carbobenzoxy), FMOC (9-fluorenylmethoxycarbonyl), MSOC (2-methanesulfenylethoxycarbonyl).

Particularly exemplary of the N-protected amino acids are those derived from the following amino acids:

(1) aliphatic amino acids: glycine, alanine, valine, leucine, isoleucine;

(2) hydroxylated amino acids: serine, threonine;

(3) sulfuretted amino acids: cysteine, methionine;

(4) dicarboxylic amino acids and their amides: aspartic acid, asparagine, glutamic acid, glutamine;

(5) amino acids with two basic groups: lysine, arginine, histidine;

(6) aromatic amino acids: phenylalanine, tyrosine, tryptophan;

(7) imino acids: proline, hydroxyproline.

Among all those exemplary compounds indicated above, the process of the invention is especially applicable to the following:

Salicylic acid and 4-hydroxy benzoic acid;

Acetic acid, propionic acid and derivatives thereof substituted by a hydroxy, halogen, aryl or aryloxy group;

Benzoic acid and derivatives thereof substituted by a $C_1$–$C_4$ alkyl group, an acetoxy group or an acetamido group;

Nicotinic acid;

N-protected amino acids.

The process of the present invention thus comprises contacting at least one of the above indicated carboxylic acids in salified form, with at least one halogenated derivative or organic halocompound, which may be represented by the general formula (III):

$$R_7\text{—}X \qquad (III)$$

in which X is a halogen atom which must not be in the vinyl or alkynyl position; and $R_7$ is an optionally substituted straight or branched, saturated or unsaturated, acyclic aliphatic radical; a monocyclic or polycyclic, saturated or unsaturated, cycloaliphatic radical; or a straight or branched, saturated or unsaturated aliphatic radical bearing a cyclic substituent.

The halogen atom is advantageously chlorine, bromine or iodine, but chlorine and bromine are the preferred.

The radical $R_7$ is preferably:

(1) A straight or branched alkyl, alkenyl, alkadienyl or alkynyl radical, preferably having from 1 to 12 carbon atoms, with the proviso that the hydrocarbon chain may optionally be interrupted by one of the following groups:

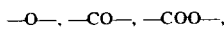

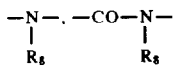

wherein $R_8$ is a hydrogen atom or an alkyl radical having from 1 to 4 carbon atoms, or a cyclohexyl or phenyl radical, and/or may be substituted by one of the following Y substituents: an —OH group, a —COOH group, a —CHO group, and —$NO_2$ group, a —C≡N group, a nonquaternizable or N-protected amino group, a halogen atom, preferably chlorine or bromine, or a —$CF_3$ group.

Exemplary $R_7$ aliphatic radicals include methyl, ethyl, propyl, isopropyl, butyl, isobutyl, sec-butyl, tert-butyl, 2-ethylbutyl, pentyl, isopentyl, neopentyl, tert-pentyl, 2-methylpentyl, hexyl, 2-ethylhexyl; allyl, 3-methyl-2-butenyl, 3-hexenyl; methoxymethyl or acetamidomethyl radicals.

(2) A cycloalkyl or cycloalkenyl radical, preferably having 5 to 7 carbon atoms, optionally bearing one or more Y substituents as indicated above and/or one or more Z substituents, such as a straight or branched alkyl radical having from 1 to 4 carbon atoms, a straight or branched alkoxy radical having from 1 to 4 carbon atoms or a radical of the formulae:

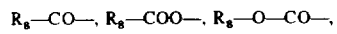

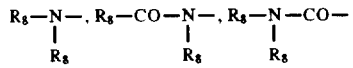

wherein $R_8$ is as defined above; such radicals may be polycyclic, and of the "bridged" type.

Exemplary $R_7$ cycloaliphatic radicals include the cyclohexyl radical and the cyclohex-1-enyl radical.

(3) A straight or branched, saturated or unsaturated, acyclic aliphatic radical as specified in (1), bearing a cyclic substituent. By the term "cyclic" is intended a saturated, unsaturated or aromatic, carbocyclic or heterocyclic ring member.

The acyclic aliphatic radical may be bonded to the ring via a simple valence bond or by one of the following groups:

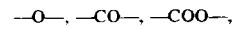

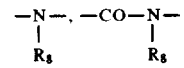

in which $R_8$ is as defined above.

Exemplary such ring members include:

(a) A monocyclic or polycyclic, saturated or unsaturated, cycloaliphatic radical as specified under (2);

(b) A phenyl, tolyl or xylyl radical, optionally bearing one or more Y or Z substituents;

(c) A saturated, unsaturated or aromatic, monocyclic heterocyclic radical with one or more oxygen, nitrogen or sulfur atoms as the hetero atoms, containing 4 to 6 atoms in the ring and optionally bearing one or more Y or Z substituents as defined above.

Exemplary such heterocyclic radicals include pyrrolidinyl, imidazolidinyl, piperidyl, furyl, pyrrolyl, thienyl, isoazolyl, furazanyl, isothiazolyl, imidazolyl, pyrazolyl, pyridyl, pyridazinyl, or pyrimidinyl radicals;

(d) A radical comprising a plurality or chain of 2 to 4 groups as specified under the above (a) and/or (b) and/or (c), interconnected via a simple valence bond and/or by one of the following groups:

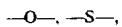

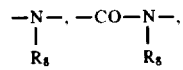

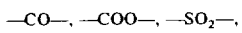

and/or at least one alkylene or alkylidene radical having from 1 to 4 carbon atoms, and wherein $R_8$ is a hydrogen atom, an alkyl radical having from 1 to 4 carbon atoms, or a cyclohexyl or phenyl radical.

Exemplary thereof are diphenyl, 1,1'-methylenediphenyl, 1,1'-oxydiphenyl, (4-carboxy-4-phenoxy)phenyl, methylene-3,4-dioxyphenyl, 2-acetylphenyl, 4-acetylphenyl, 2-benzoylphenyl, 4-benzoylphenyl, 3-benzoyloxy-2-ethylphenyl, 2-acetoxyphenyl, 4-acetoxyphenyl, 2-acetamidophenyl and 4-acetomidophenyl radicals;

(e) An aromatic radical comprising a structure of 2 or 3 carbocyclic and/or heterocyclic aromatic ring members which together constitute orthocondensed systems.

The aromatic rings are preferably benzene and pyridine rings.

Exemplary such polycylic aromatic radicals include anthryl, quinolyl, naphthyridinyl, benzofuranyl and indolyl radicals.

Preferred $R_7$ cyclo or arylaliphatic radicals bearing a cyclic substituent include cyclohexylmethyl, cyclohexylbutyl, benzyl, 2-phenylethyl, 2-|4-(2-butyl) phenyl|ethyl, styryl, α-phenylcyclohexylmethyl, phenoxymethyl and phenoxyethyl radicals.

In the definition of the radical $R_7$ comprising the halogenated compound of formula (III), it was indicated that same may have one or more Y or Z substituents. By "more" is intended a total number typically no greater than 3.

The preferred radicals $R_7$ include:

A straight or branched alkyl radical having from 1 to 8 carbon atoms, such as the methyl, ethyl, propyl isopropyl, butyl, isobutyl, sec-butyl, tert-butyl 2-ethylbutyl, pentyl, isopentyl, neopentyl, tert-pentyl 2-methylpentyl, hexyl or 2-ethylhexyl radicals;

A straight or branched alkenyl radical having from 2 to 8 carbon atoms and having a site of ethylenic unsaturation in the beta position to the X group, for example the allyl radical, the 3-methyl-2-butenyl radical or the 3-hexenyl radical;

A cyclohexyl radical optionally substituted by a straight or branched alkyl radical having from 1 to 4 carbon atoms;

An arylalkyl radical having the following formula:

wherein m is an integer ranging from 1 to 4 and preferably equal to 1.

The following compounds are preferred examples of the halocompounds of formula (III):

Methyl bromide,
Ethyl bromide,
n-Propyl bromide,
Bromoisopropane,
Bromobutane,
Bromohexane,
Bromoheptane,
Bromooctane,
1-Bromo-2-methylbutane,
1-Bromo-3-methylbutane,
2-Bromo-2-methylbutane,
Allyl bromide,
Allyl chloride,
Crotyl chloride,
3-Chloro-2-methylpropene,
1-Chloro-2-butene,
1-Chloro-3-methyl-2-butene,
Prenyl bromide,
Geranyl bromide,
Geranyl chloride
α-Bromoacetone,
α,α-Dibromoacetone,
α-Chloroacetone,
α,α-Dichloroacetone,
Methyl-α-bromopropionate,
Butyl-α-bromopropionate,
Methyl-α-chloropropionate,
Butyl-α-chloropropionate,
Bromocyclobutane,
Bromocyclopentane,
Bromocyclohexane,
Bromocycloheptane,
(Bromomethyl)cyclopropane,
(2-Chloromethyl)pyridine,
(3-Chloromethyl)pyridine,
(4-Chloromethyl)pyridine,
Benzyl bromide,
Benzyl chloride,
4-Chloromethylstilbene,
(1-Bromomethyl)naphthalene,
(2-Bromomethyl)naphthalene.

Insofar as the halide is concerned, whether a chloride or a bromide, this is selected depending on the type of hydrocarbon from which the halide is derived, and economic requirements.

A bromine compound may be used in all instances in carrying out the process of the invention.

However, since chlorides are less expensive, preferably these will be used, but they cannot always be used. It is not possible according to the invention to use a chloride if a site of unsaturation is present on the hydrocarbon chain bearing the chlorine atom, in the alpha-position relative to the latter (such site of unsaturation may be a double or triple bond). Benzyl chloride may advantageously be used, for example.

As indicated above, the radical $R_7$ may bear a different halogen atom.

Thus, the process of the invention permits the preparation of diesters of carboxylic acids.

It should be appreciated that the halogen atoms must not be present on the same carbon atom.

Diesters of a carboxylic acid may be prepared in cases where the following are used:

Any type of dibrominated compounds, such as dibromoethane, 1,2-dibromoethane, 1,2-dibromopropane, 1,3-dibromopropane, 1,2-dibromobutane, 1,3-dibromobutane, 1,4-dibromobutane, 1,6-dibromohexane, 1,4-dibromo-2-butene, 1,4-dibromobutyne or bis-1,4-(bromomethyl)benzene.

Dichlorinated compounds, particularly dichloromethane, dichloroethane, 1,4-dichloro-2-pentene or bis-1,4-(chloromethyl)benzene;

Mixed brominated and chlorinated compounds, such as bromochloroethane, 1-bromo-3-chloropropane or 1-bromo-4-chlorobutane.

In the process of the present invention it is also possible to prepare a diester when the Q radical of the carboxylic acid, in salified form, in formula (I) bears a different —COOM— group.

It will also be appreciated that the process of the invention may also be applied to the esterification of polycarboxylic acids, whatever the position of the carboxylate group, whether it is borne by a ring and/or present on an aliphatic hydrocarbon chain.

A catalyst, namely, a phase transfer catalyst, is employed in the process of the invention.

Known phase transfer catalysts may thus be used, particularly those described in Jerry March, *Advanced Organic Chemistry*, 3rd Edition, p. 320 ff, John Wiley & Sons (1985).

The preferred catalysts for the process of the invention are the onium salts and more particularly quaternary ammonium and/or phosphonium salts.

Exemplary onium salts useful for the process of the invention are those in which the onium ions are derived, particularly, from nitrogen, phosphorus, arsenic, sulfur, selenium, oxygen, carbon or iodine and coordinated with hydrocarbon radicals. Such onium ions derived from nitrogen, phosphorus or arsenic will be quadricoordinated, those derived from sulfur, selenium, oxygen, carbon or S=O tricoordinated, and those derived from iodine dicoordinated.

The hydrocarbon radicals coordinated with these various elements include the alkyl, alkenyl, aryl, cycloalkyl or aralkyl radicals and optionally substituted such radicals; two coordinated hydrocarbon radicals may together form a single divalent radical.

The nature of the anions associated with these organic cations is not critical. Any "hard" or "borderline" bases constitute suitable anions.

By "hard" or "borderline" is intended any anion within the classic definition given in R. Pearson, *Journal of Chem. Ed.*, 45, pages 581–587 (1968).

Exemplary of the onium ions which may be used in the process of the present invention, those having one of the following general formulae are particularly representative:

 (IV)

 (V)

 (V')

 (VI)

-continued

(VII)

wherein W is N, P or As; Q is S, O, Se, S=O or C; $R_9$, $R_{10}$, $R_{11}$ and $R_{12}$, which may be the same or different, are each a straight or branched alkyl radical having from 1 to 16 carbon atoms, optionally substituted by one or more phenyl, hydroxyl, halogen, nitro, alkoxy or alkoxycarbonyl radicals or atoms, the alkoxy radicals having from 1 to 4 carbon atoms, a straight or branched alkenyl radical having from 2 to 12 carbon atoms, an aryl radical having from 6 to 10 carbon atoms, optionally substituted by one or more alkyl radicals having from 1 to 4 carbon atoms, an alkoxy or alkoxycarbonyl radical, the alkoxy radical having from 1 to 4 carbon atoms, or a halogen atom, with the proviso that two of the radicals $R_9$ to $R_{12}$ may together form a straight or branched alkylene, alkenylene or alkadienylene radical having from 3 to 6 carbon atoms; $R_{13}$, $R_{14}$, $R_{15}$, and $R_{16}$, which may be the same or different, are each a straight or branched alkyl radical having from 1 to 4 carbon atoms, with the proviso that the radicals $R_{15}$ and $R_{16}$ may together form an alkylene radical having from 3 to 6 carbon atoms and the radicals $R_{14}$ and $R_{15}$ or $R_{15}$ and $R_{16}$ may together form an alkylene, alkenylene or alkadienylene radical having 4 carbon atoms and constituting a nitrogen heterocycle with the nitrogen atom from which they depend; and $R_{17}$ is a divalent radical which, together with the two nitrogen atoms from which it depends, constitutes a ring of 4 to 6 atoms which may include one or more nitrogen, sulfur and/or oxygen bridging atoms, such ring optionally being substituted by one or more radicals, e.g., $R_9$.

Exemplary of the "hard" or "borderline" bases which may constitute the anion of the onium salts, the following ions are representative: $F^-$, $ClO_4^-$, $PF_6^-$, $BF_4^-$, $SnCl_6^-$, $SbCl_6^-$, $B(Ph)_4^-$, $PO_4^-$, $HPO_4^{2-}$, $H_2PO_4^-$, $CH_3SO_3^-$, $Ph-SO_3^-$, $HSO_4^-$, $NO_3^-$, $SO_4^{2-}$, $Cl^-$, $Br^-$, $I^-$, $OH^-$, with Ph being a phenyl radical, and any other anions within PEARSON's definition of a "hard" or "borderline" base.

For reasons of convenience in use, the anions are advantageously selected from among $PO_4^{3-}$, $HPO_4^{2-}$, $H_2PO_4^-$, $CH_3SO_3^-$, $Ph-SO_3^-$, $NO_3^-$, $SO_4^{2-}$, $PF_6^-$, $Cl^-$, $Br^-$ and $I^-$. It is particularly advantageous to use $Br^-$ and $Cl^-$ anions.

The following cations are exemplary of the onium ions of formula (IV):
Tetramethylammonium,
Triethylmethylammonium,
Tributylmethylammonium,
Trimethylpropylammonium,
Tetraethylammonium,
Tetrabutylammonium,
Dodecyltrimethylammonium,
Methyltrioctylammonium,
Heptyltributylammonium,
Tetrapropylammonium,
Tetrapentylammonium,
Tetrahexylammonium,
Tetraheptylammonium,
Tetraoctylammonium,
Tetradecylammonium,
Butyltripropylammonium,
Methyltributylammonium,
Pentyltributylammonium,
Methyldiethylpropylammonium,
Ethyldimethylpropylammonium,
Tetradodecylammonium,
Tetraoctadecylammonium,
Hexadecyltrimethylammonium,
Benzyltrimethylammonium,
Benzyldimethylpropylammonium,
Benzyldimethyloctylammonium,
Benzyltributylammonium,
Benzyltriethylammonium,
Phenyltrimethylammonium,
Benzyldimethyltetradecylammonium,
Benzyldimethylhexadecylammonium,
Dimethyldiphenylammonium,
Methyltriphenylammonium,
2-Butenyltriethylammonium,
N,N-Dimethyl-tetramethyleneammonium,
N,N-Diethyl-tetramethyleneammonium,
Tetramethylphosphonium,
Tetrabutylphosphonium,
Ethyltrimethylphosphonium,
Trimethylpentylphosphonium,
Octyltrimethylphosphonium,
Dodecyltrimethylphosphonium,
Trimethylphenylphosphonium,
Diethyldimethylphosphonium,
Dicyclohexyldimethylphosphonium,
Dimethyldiphenylphosphonium,
Cyclohexyltrimethylphosphonium,
Triethylmethylphosphonium,
Methyltri(isopropyl)phosphonium,
Methyltri(n-propyl)phosphonium,
Methyltri(n-butyl)phosphonium,
Methyltri(2-methylpropyl)phosphonium,
Methyltricyclohexylphosphonium,
Methyl triphenylphosphonium,
Methyltribenzylphosphonium,
Methyltri(4-methylphenyl)phosphonium,
Methyltrixylylphosphonium,
Diethylmethylphenylphosphonium,
Dibenzylmethylphenylphosphonium,
Ethyltriphenylphosphonium,
Tetraethylphosphonium,
Ethyltri(n-propyl)phosphonium,
Triethylpentylphosphonium,
Hexadecyltributylphosphonium,
Ethyltriphenylphosphonium,
n-Butyltri(n-propyl)phosphonium,
Butyltriphenylphosphonium,
Benzyltriphenylphosphonium,
(β-Phenylethyl)dimethylphenylphosphonium,
Tetraphenylphosphonium,
Triphenyl(4-methylphenyl)phosphonium,
Tetrakis(hydroxymethyl)phosphonium,
Tetraphenylarsonium.

Exemplary of the cations of formulae (V) and (V'), the following are representative:
N-Methylpyridinium,
N-Ethylpyridinium,
N-Hexadecylpyridinium,
N-Methylpicolinium,
1,2,4-Triphenyl triazolium.

Exemplary of the onium ions of formula (VI) are the following cations:
Trimethylsulfonium,
Triethylsulfonium,
Triphenylsulfonium,
Trimethylsulfoxonium,
Triphenylcarbenium,
Triethyloxonium.

And exemplary onium anions of formula (VII) are the following cations:

Diphenyliodonium,
4,4'-Dimethoxy diphenyliodonium (or the compounds described in *JACS*, 81, 342 (1958)),
2-Carboxylate diphenyliodonium.

Of the suitable onium ions according to this invention, the quaternary ammonium ions, quaternary phosphonium ions, sulfonium ions and iodonium ions will generally be preferred.

Ammonium ions where the four groups are alkyl radicals having from 1 to 5 carbon atoms or a benzyl radical are particularly suitable.

As regards the anion, $Br^-$ or $Cl^-$ will preferably be selected.

Particularly suitable catalysts according to the invention include tributybenzylammonium or phosphonium chloride or bromide, tetramethylammonium or phosphonium chloride or bromide, tetraethylammonium or phosphonium chloride or bromide, or tetrabutylammonium or phosphonium chloride or bromide.

The onium salt may be introduced in the subject process in the solid state or in the form of a solution in a solvent therefor, typically water.

In the process of the invention, the reaction in which the carboxylic acid salt is esterified is carried out in the presence of a phase transfer catalyst; the various reagents are generally employed in the proportions indicated below.

The molar ratio of the number of carboxylate functions in the carboxylic acid to the number of reacting halogen atoms in the halogenated derivative preferably ranges from 0.5 to 2.0:1.0. It is more preferably in the region of 1.0:1.0. When one departs from the preferred value and uses a deficiency of halogenated derivative, the reaction is less complete. In cases where there is an excess of the halogenated derivative, that excess has to be separated at the end of the reaction.

As regards the amount of catalyst used, this advantageously varies such that the molar ratio of catalyst to carboxylic acid salt ranges from 0.01 to 0.50:1.0 and preferably from 0.05 to 0.2:1.0. The upper limit is not critical and may be greatly exceeded without any disadvantage, as the catalyst can optionally be recycled at the end of the reaction.

As indicated above, the reaction is carried out in an aqueous medium without any organic solvent present.

The carboxylic acid salt is dissolved in water. Its concentration is not critical and depends solely on its solubility in water.

In a preferred embodiment of the invention, the highest possible concentration is selected. For example, the concentration of carboxylic acid salt in water may be up to 50% by weight. It is desirably from 30% to 50% by weight, but very low concentrations can nevertheless be used.

The amount of water present in the reaction medium generally ranges from 50% to preferably 100% of the total weight of reagents involved.

In another preferred embodiment of the present invention, a salt of a carboxylic acid is esterified by reacting such salt with a haloderivative of an aliphatic hydrocarbon, cycloaliphatic hydrocarbon or aliphatic hydrocarbon bearing a cyclic substituent, in an aqueous reaction medium, in the presence of a phase transfer catalyst; preferably the salt of the carboxylic acid, in aqueous solution, is progressively introduced into the haloderivative.

In a convenient embodiment of the invention, a sediment is prepared comprising the halogenated derivative and the catalyst for the reaction.

The carboxylic acid salt in aqueous solution is then added to the medium.

The carboxylic acid salt is preferably added gradually. The period of addition may vary widely, from 5 minutes to 8 hours and, preferably, from 20 minutes to 4 hours.

The temperature at which the process of the invention is carried out advantageously ranges from 50° to 120° C.

A temperature of from 70° to 90° C. is preferable.

The pressure for the reaction is not critical and is generally atmospheric.

It is preferable to conduct the reaction under autogenous pressure to attain the above temperatures.

The duration of the reaction depends on the reaction temperature and the desired conversion rate. When the temperature is selected within the preferred range, the duration may vary widely, for example from 15 minutes to 10 hours.

At the end of the reaction, the carboxylic acid ester constitutes the organic phase which can be separated from the aqueous phase.

The organic phase may also contain the catalyst and the unreacted halogenated derivative in the event that an excess amount is used.

The aqueous phase recovered contains a salt in the form of a halide derived from the metal cation emanating from the carboxylic acid and from the anion which is the halide derived from the halogenated derivative.

The ester obtained may be separated from the organic phase by conventional techniques, such as distillation or extraction by means of an appropriate solvent.

The process of the invention is very patentable suited for the preparation of esters of salicylic acid, particularly alkyl or alkenyl salicylates such as methyl, ethyl, isopropyl, amyl or isoamyl salicylate, 2-methylpentyl salicylate, n-hexyl salicylate, 2-ethylbutyl salicylate, 2-ethylhexyl salicylate, 2-methyl 2-butenyl salicylate or cis-3-hexenyl salicylate; substituted alkyl or alkenyl salicylates, such as glycol, monomethylamine or beta-isopropoxyethyl substituted salicylate; cycloalkyl or cycloalkenyl salicylates, optionally substituted, such as cyclohexyl salicylate, 2-isopropyl cyclohexyl salicylate, 3,3,5-trimethylcyclohexyl salicylate or bornyl salicylate; and arylalkyl salicylates such as benzyl salicylate.

The present invention is also applicable for the preparation of esters of o- m- or p-aminosalicyclic acid. Exemplary thereof are menthyl o-amino and monsalicylate, menthyl p-amino and monosalicylate and allyl p-amino and monosalicylate.

The process of this invention is also well adapted for the preparation of esters of p-hydroxybenzoic acid. Exemplary thereof are methyl p-hydroxybenzoate and propyl p-hydroxybenzoate.

One significant advantage of the process of the present invention is that it permits esters of hydroxybenzoic acids to be obtained with a good rate of conversion from the starting acid, and provides good selectivity in respect of the possible O-alkylation reaction.

The process of the invention is also especially suitable for the preparation of the alkyl, cyclohexyl and benzyl esters of acetic acid, propionic acid and derivatives thereof bearing a hydroxy, halogen, aryl or aryloxy substituent; benzoic acid and derivatives thereof bearing a $C_1$–$C_4$ alkyl, acetoxy or acetamido substituent; nicotinic acid and N-protected amino acids.

In order to further illustrate the present invention and the advantages thereof, the following specific examples are given, it being understood that same are intended only as illustrative and in nowise limitative.

In said examples to follow, the abbreviations below have the following respective definitions:

$$TT_H = \frac{\text{number of moles of halogenated derivative converted}}{\text{number of moles of halogenated derivative introduced}} \%$$

$$TT_A = \frac{\text{number of moles of carboxylic acid salt recovered}}{\text{number of moles of carboxylic acid salt introduced}} \%$$

$$RR_H = \frac{\text{number of moles of carboxylic acid ester formed}}{\text{number of moles of halogenated derivative introduced}} \%$$

$$RR_A = \frac{\text{number of moles of carboxylic acid formed}}{\text{number of moles of carboxylic acid salt introduced}} \%$$

$$RT_H = \frac{\text{number of moles of carboxylic acid ester formed}}{\text{number of moles of halogenated derivatives converted}} \%$$

$$RT_A = \frac{\text{number of moles of carboxylic acid ester formed}}{\text{number of moles of carboxylic acid salt converted}} \%$$

The Examples 1 to 13 illustrate the preparation of various esters of carboxylic acids.

EXAMPLE 1

Preparation of benzyl acetate

A 250 ml glass reaction was used, fitted with an agitating system, a temperature control means, means for introducing the reagent and a cooler, and equipped with a heating system. 63.25 g (0.5 mol) of benzyl chloride, 10 ml of water and 15.6 g of tributylbenzylammonium chloride (0.05 mol) were introduced into the reactor and heated to 80° C.

A sodium acetate solution, prepared from 30 g of acetic acid (0.5 mol), 25 ml of water and 50 ml of an aqueous solution of 10N caustic soda, was introduced gradually at 80° C., over 4 hours, 45 minutes.

The reaction medium was then maintained at 80° C. for one additional hour.

Upon completion of the reaction and after cooling, the organic phase containing benzyl acetate was separated from the catalyst and from the aqueous phase containing sodium chloride.

68 g of an oil comprising benzyl acetate was recovered from this organic layer after it had been washed with water 3 times, each time employing 100 ml of water.

The presence of benzyl acetate was confirmed by NMR and mass spectrography.

The results obtained were as follows:

(a) Conversion rate ($TT_H$) of benzyl chloride=84%

(b) Yield of benzyl acetate relative to benzyl chloride= $RT_H$=92%

EXAMPLE 2

Preparation of benzyl acetate 63.25 g (0.5 mol) of benzyl chloride, 10 ml of water and 20.3 g of methyltriphenylphosphonium iodide were introduced into the reactor described above and heated to 80° C.

A sodium acetate solution, prepared from 30 g of acetic acid (0.5 mol), 25 ml of water and 50 ml of an aqueous solution of 10N caustic soda, was introduced gradually at 80° C., over 1 hour, 20 minutes.

The reaction medium was then maintained at 80° C. for one additional hour.

Upon completion of the reaction, the benzyl acetate was separated in the same manner as in the previous example.

The presence of benzyl acetate was confirmed by NMR and mass spectrography.

The results obtained were as follows:

(a) Conversion rate ($TT_H$) of benzyl chloride=100%

(b) Conversion rate ($TT_A$) of sodium acetate=100%

(c) Yield of benzyl acetate relative to benzyl chloride= $RT_H$=80%

(d) Yield of benzyl acetate relative to sodium acetate= $RT_A$=80%

EXAMPLE 3

Preparation of allyl salicylate 60.5 g of allyl bromide, 10 ml of water and 15.6 g of tributylbenzyl ammonium chloride (0.05 mol) were introduced into the reactor described above and heated to 60° C.

A sodium salicylate solution, prepared from 69 g of salicylic acid (0.5 mol), 25 ml of water and 50 ml of an aqueous solution of 10N caustic soda, was introduced gradually at 60° C., over 6 hours.

The reaction medium was then maintained at 60° C. for an additional 20 minutes.

Upon completion of the reaction, the allyl salicylate was separated and in the same manner as in the previous example.

The presence of allyl salicylate was confirmed by NMR and mass spectrography.

The results obtained were as follows:

(a) Conversion rate ($TT_H$) of allyl bromide=100%

(b) Conversion rate ($TT_A$) of sodium salicylate=100%

(c) Yield of allyl salicylate relative to allyl bromide= $RR_H$=90%

(d) Yield of allyl salicylate relative to sodium salicylate= $RR_A$=90%

EXAMPLE 4

Preparation of benzyl salicylate

A 500 ml glass reactor was used, fitted with an agitating system, a temperature control means, means for introducing the reagent and a cooler, and equipped with a heating system. 63.3 g (0.5 mol) of benzyl chloride and the catalyst, which was tetrabutylammonium bromide in amounts of 10 molar % of the sodium salicylate, were introduced into the reactor and heated to 80° C.

20 ml of water were added and 80 g (0.5 mol) of sodium salicylate, dissolved in 60 ml of water, were introduced gradually at 80°.

The solution was poured into the benzyl chloride containing the catalyst, over 2 hours, 35 minutes.

The reaction medium was then maintained to 80° C. for 3 hours, 30 minutes.

Upon completion of the reaction and after cooling, the organic phase (64 ml) containing the benzyl salicylate was separated from the catalyst and from the aqueous phase (58 ml) containing sodium chloride.

The organic layer was washed with water 3 times, each time employing 50 ml of water, then the benzyl salicylate was recovered therefrom by distillation at 148° C. at 2.5 mm of mercury.

The results obtained were as follows:

(a) Conversion rate ($TT_A$) of sodium salicylate=98.6%

(b) Conversion rate ($TT_H$) of benzyl chloride=99.8%

(c) Yield of benzyl salicylate relative to sodium salicylate=$RR_A$=92.5% $RT_A$=93.8%

(d) Yield of benzyl salicylate relative to benzyl chloride= $RR_H$=92.7% $RT_H$=93.9%

EXAMPLES 5, 6 AND 7

The procedure of Example 4 was repeated, without employing any catalyst (Example 5).

Other tests were carried out using a different type of catalyst, namely:

(i) tributylbenzylammonium chloride BzBu$_3$NCl (Example 6);

(ii) tetraethylammonium bromide Et$_4$NBr (Example 7).

The amounts of reagents used, the operating conditions and the results obtained are reported in the Table below:

(a) Conversion rate (TT$_H$) of benzyl chloride=100%

(b) Conversion rate (TT$_A$) of sodium phenoxyacetate=100%

(c) Yield of benzyl phenoxyacetate relative to benzyl chloride=RR$_H$=100%

TABLE

| Example | SNa | BzCl | Molar/ratio SNa/BzCl | Water | Catalyst | Pouring SNa | Temperature °C. | Reaction time | Yields/SNa TT$_A$ | RR$_A$ | RT$_A$ | Yields/BzCl TT$_H$ | RR$_H$ | RT$_H$ |
|---|---|---|---|---|---|---|---|---|---|---|---|---|---|---|
| 5 | 80 g 0.5 mol | 63.3 g 0.5 mol | 1 | 120 ml | none | 0 h, 30 min | 80° C. | 3 h, 30 min | 62.0% | 34.2% | 55.1% | 97.4% | 34.2% | 35.1% |
| 6 | 80 g 0.5 mol | 63.3 g 0.5 mol | 1 | 120 ml | BzBu$_3$NCl 10% | 5 h, 45 min | 80° C. | 3 h, 30 min | 96.6% | 93.4% | 97.0% | 99.8% | 93.4% | 93.6% |
| 7 | 80 g 0.5 mol | 63.3 g 0.5 mol | 1 | 120 ml | Et$_4$NBr 10% | 0 h, 20 min | 80° C. | 3 h, 30 min | 65.2% | 47.3% | 72.5% | 98.5% | 47.3% | 48.0% |

The following abbreviations appear in the Table:
SNa: sodium salicylate
BZCl: benzyl chloride
The very poor yields obtained in the absence of catalysts are apparent.

EXAMPLE 8
Preparation of benzyl salicylate 80 g (0.5 mol) of sodium salicylate dissolved in 60 ml of water and the catalyst, which was tetrabutylammonium bromide in amounts of 10 molar % of the sodium salicylate, were introduced into a glass reactor as described in Example 1 and heated to 70° C.

20 ml of water were added and 63.3 g (0.5 mol) of benzyl chloride were introduced gradually at 80° C.

The benzyl chloride was poured into the sodium salicylate solution containing the catalyst over 2 hours, 30 minutes.

The reaction medium was then maintained at 70° C. for 1 hour and at 80° C. for 2 hours.

When the reaction was complete and the medium had cooled, the organic phase containing the benzyl salicylate was separated from the catalyst and from the aqueous phase, containing sodium chloride.

The organic phase was treated as in Example 1.

The results obtained were as follows:

(a) Conversion rate (TT$_A$) of sodium salicylate=86.8%

(b) Conversion rate (TT$_H$) of benzyl chloride=100%

(c) Yield of benzyl salicylate relative to sodium salicylate=RR$_A$=76.7% RT$_A$=88.4%

(d) Yield of benzyl salicylate relative to benzyl chloride=RR$_H$=76.7% RT$_H$=76.7%

EXAMPLE 9
Preparation of benzyl phenoxyacetate 21 g of benzyl chloride, 10 ml of water and 4.68 g of tributylbenzylammonium chloride were introduced into the reactor described above and heated to 80° C.

A sodium phenoxyacetate solution, prepared from 22.8 g of phenoxyacetic acid, 130 ml of water and 15 ml of an aqueous solution of 10N caustic soda, was introduced gradually at 80° C., over 1 hour.

The reaction medium was then maintained at 80° C. for an additional 2 hours, 15 minutes.

When the reaction was complete, the benzyl phenoxyacetate was separated in the same manner as in the previous example.

The presence of benzyl phenoxyacetate was confirmed by NMR and mass spectrography.

The results obtained were as follows:

(d) Yield of benzyl phenoxyacetate relative to sodium phenoxyacetate=RR$_A$=100%

EXAMPLE 10
Preparation of benzyl nicotinate 25.3 g of benzyl chloride, 10 ml of water and 6.24 g of tributylbenzylammonium chloride were introduced into the reactor described above and heated to 80° C.

A sodium nicotinate solution, prepared from 24.6 g of nicotinic acid, 75 ml of water and 20 ml of an aqueous solution of 10N caustic soda, was introduced gradually at 80° C., over 45 minutes.

The reaction medium was then maintained at 100° C. for an additional 3 hours.

When the reaction was complete, the benzyl nicotinate was separated in the very same manner as in the previous example.

The presence of benzyl nicotinate was confirmed by NMR and mass spectrography.

The results obtained were as follows:

(a) Conversion rate (TT$_H$) of benzyl chloride=100%

(b) Conversion rate (TT$_A$) of sodium nicotinate=100%

(c) Yield of benzyl nicotinate relative to benzyl chloride=RR$_H$=100%

(d) Yield of benzyl nicotinate relative to sodium nicotinate=RR$_A$=100%

EXAMPLE 11
Preparation of benzyl lactate 63.25 g (0.5 mol) of benzyl chloride, 10 ml of water and 15.6 g (0.05 mol) of tributylbenzylammonium chloride were introduced into the reactor described above and heated to 90° C.

A sodium lactate solution, prepared from 45 g (0.5 mol) of lactic acid, 25 ml of water and 50 ml of an aqueous solution of 10N caustic soda, was introduced gradually at 90° C., over 1 hour.

The reaction medium was then maintained at 90° C. for one additional hour.

When the reaction was complete, the benzyl lactate was separated in the same manner as in the previous example.

The presence of benzyl lactate was confirmed by NMR and mass spectrography.

The results obtained were as follows:

(a) Conversion rate ($TT_H$) of benzyl chloride=100%

(b) Conversion rate ($TT_A$) of sodium lactate=100%

(c) Yield of benzyl lactate relative to benzyl chloride= $RR_H$=90%

(d) Yield of benzyl lactate relative to sodium lactate= $RR_A$=90%

EXAMPLE 12

Preparation of butyl acetate 41 g (0.3 mol) of bromobutane, 10 ml of water and 9.36 g (0.03 mol) of tributylbenzylammonium were introduced into the reactor described above and heated to 85° C.

A sodium acetate solution, prepared from 18 g (0.3 mol) of acetic acid, 35 ml of water and 30 ml of an aqueous solution of 10N caustic soda, was introduced gradually at 85° C., over 3 hours, 45 minutes.

The reaction medium was then maintained at 85° C. for one additional hour.

When the reaction was complete, the butyl acetate was separated in the same manner as in the previous example.

The presence of butyl acetate was confirmed by NMR and mass spectrography.

The results obtained were as follows:

(a) Conversion rate ($TT_H$) of bromobutane=100%

(b) Conversion rate ($TT_A$) of sodium acetate=100%

(c) Yield of butyl acetate relative to bromobutane=$RR_H$=100%

(d) Yield of butyl acetate relative to sodium acetate=$RR_A$=100%

EXAMPLE 13

Preparation of ethylene diacetate 94 g of dibromoethane, 10 ml of water and 15.6 g of tributylbenzylammonium chloride (0.05 mol) were introduced into the reactor described above, and heated to 100° C.

A sodium acetate solution, prepared from 60 g of acetic acid, 100 ml of water and 100 ml of an aqueous solution of 10N caustic soda, was introduced gradually at 100° C., over 1 hour, 40 minutes.

The reaction medium was then maintained at 100° C. for an additional 1 hour, 30 minutes.

When the reaction was complete, the ethylene diacetate was separated in the manner as in the previous example.

The presence of ethylene diacetate was confirmed by NMR and mass spectrography.

The results obtained were as follows:

(a) Conversion rate ($TT_H$) of dibromoethane=100%

(b) Conversion rate ($TT_A$) of sodium acetate=100%

(c) Yield of ethylene diacetate relative to dibromoethane= $RR_H$=64%

(d) Yield of ethylene diacetate relative to sodium acetate= $RR_A$=64%

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of an ester of an aromatic carboxylic acid comprising the steps of:

(a) introducing a salt of a carboxylic acid into an aqueous reaction medium containing an organic halocompound; and (b) reacting said carboxylic acid salt with said organic halocompound at a temperature ranging from 50° C. to 120° C. in the presence of a catalytically effective amount of a phase transfer catalyst to produce a product comprising an aqueous phase and an organic phase containing the ester, wherein water is not removed during said reacting step (b).

2. The process as defined by claim 1, said organic halocompound comprising a halogenated aliphatic hydrocarbon, a halogenated cycloaliphatic hydrocarbon, a halogenated cycloaliphatic hydrocarbon, a halogenated aliphatic hydrocarbon bearing a cyclic substituent, or derivative thereof.

3. The process as defined by claim 1, said carboxylic acid salt having the formula (I):

in which Q is an optionally substituted hydrocarbon radical having from 1 to 40 carbon atoms; M is a metal; and w is a number representing the valence or multiple thereof of the metal M.

4. The process as defined by claim 3, wherein formula (I), Q is an optionally substituted hydrocarbon radical having from 1 to 20 carbon atoms and M is a Group Ia or IIa metal cation, or an ammonium radical.

5. The process as defined by claim 4, wherein formula (I), Q is a substituted or unsubstituted, straight or branched chain saturated or unsaturated acyclic aliphatic such hydrocarbon radical, or a monocyclic or polycyclic saturated, unsaturated or aromatic carbocyclic or heterocyclic radical.

6. The process as defined by claim 5, wherein formula (I), Q is an aromatic hydrocarbon radical having the formula (II):

in which n is an integer ranging from 0 to 5; and R is $R_1$ which represents a straight or branched alkyl radical having from 1 to 6 carbon atoms, a straight or branched alkenyl radical having from 2 to 6 carbon atoms, a straight or branched alkoxy radical having from 1 to 6 carbon atoms, or one of the radicals —$R_2$—OH, —$R_2$—COOM, —$R_2$—CHO, —$R_2$—$NO_2$, —$R_2$—CN, —$R_2$—$NH_2$, —$R_2$—SH —$R_2$—X or $R_2CF_3$, wherein $R_2$ is a simple valence bond, or a saturated or unsaturated, straight or branched divalent hydrocarbon radical having from 1 to 4 carbon atoms; and X is a halogen atom.

7. The process as defined by claim 5, wherein formula (I) Q is an aromatic hydrocarbon radical having the formula (II):

in which n is an integer ranging from 0 to 5; and R is radical $R_3$ having the formula:

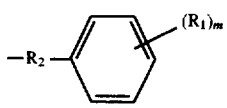

in which $R_1$ is a straight or branched alkyl radical having from 1 to 6 carbon atoms, a straight or branched alkenyl radical having from 2 to 6 carbon atoms, a straight or branched alkoxy radical having from 1 to 6 carbon atoms, or one of the radicals —$R_2$—OH, —$R_2$—COOM, —$R_2$—CHO, —$R_2$—NO$_2$, —$R_2$—CN, —$R_2$—NH$_2$—, —$R_2$—SH, —$R_2$—X or $R_2CF_3$, wherein $R_2$ is a simple valence bond, or a saturated or unsaturated, straight or branched divalent hydrocarbon radical having from 1 to 4 carbon atoms; and X is a halogen atom; m is an integer ranging from 0 to 3; or a radical having the formula:

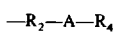

in which $R_4$ is a straight or branched alkyl radical having from 1 to 6 carbon atoms, or a radical:

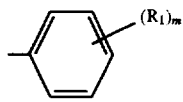

and A is a radical or group:

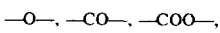

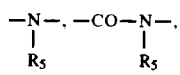

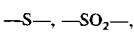

in which $R_5$ is a hydrogen atom, or a straight or branched alkyl radical having from 1 to 4 carbon atoms.

8. The process as defined by claim 6, wherein formula (II), n is greater than 1 and the radicals R are identical or different, with the proviso that two successive carbon atoms in the benzene nucleus may optionally be interconnected via a ketal bridge.

9. The process as defined by claim 5, wherein formula (I), Q is an aromatic hydrocarbon radical having the formula (II):

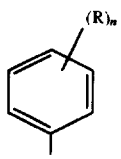

in which n is 0, 1, 2 or 3, and R is a hydrogen atom, a straight or branched alkyl or alkoxy radical having from 1 to 4 carbon atoms, a methylene or ethylene dioxy radical, an —OH or —CHO group, a phenyl or benzyl radical, or a halogen atom.

10. The process as defined by claim 5, wherein formula (I), Q is a naphthalene radical, or a substituted such naphthalene radical bearing from 1 to 4 substituents R, in which R is a straight or branched alkyl radical having from 1 to 6 carbon atoms, a straight or branched alkenyl radical having from 2 to 6 carbon atoms, a straight or branched alkoxy radical having from 1 to 6 carbon atoms, or one of the radicals —$R_2$OH, —$R_2$—COOM, —$R_2$—CHO, —$R_2$—NO$_2$, —$R_2$—CN, —$R_2$—NH$_2$, —$R_2$—SH, —$R_2$—X or —$R_2$—CF$_3$, in which $R_2$ is a simple valence bond, or a saturated or unsaturated, straight or branched divalent hydrocarbon radical having from 1 to 4 carbon atoms; and X is a halogen atom.

11. The process as defined by claim 8, wherein formula (II), two successive carbon atoms in a benzene nucleus of at least one of said radicals R are interconnected via an extranuclear methylene dioxy or ethylene dioxy bridge.

12. The process as defined by claim 5, wherein formula (I), Q is an aromatic hydrocarbon radical having the formula (II):

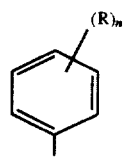

in which n is 0, 1, 2 or 3, and R is a hydrogen atom, a straight or branched alkyl radical having from 1 to 4 carbon atoms, a straight or branched alkoxy radical having from 1 to 4 carbon atoms, a methylene or ethylene dioxy radical, an —OH group, a —CHO group, a phenyl or benzyl radical, or a halogen atom.

13. The process as defined by claim 3, wherein formula (I), Q is a saturated or unsaturated carbocyclic radical, or a substituted such radical bearing from 1 to 5 substituents R, in which R is a straight or branched alkyl radical having from 1 to 6 carbon atoms, a straight or branched alkenyl radical having from 2 to 6 carbon atoms, a straight or branched alkoxy radical having from 1 to 6 carbon atoms, or one of the radicals —$R_2$OH, —$R_2$—COOM, —$R_2$—CHO, —$R_2$—NO$_2$, —$R_2$—CN, —$R_2$—NH$_2$, —$R_2$—SH, —$R_2$—X or —$R_2$—CF$_3$, in which $R_2$ is a simple valence bond, or a saturated or unsaturated, straight or branched divalent hydrocarbon radical having from 1 to 4 carbon atoms; and X is a halogen atom.

14. The process as defined by claim 3, wherein formula (I), Q is a straight or branched, saturated or unsaturated, acyclic aliphatic hydrocarbon radical, with the proviso that the hydrocarbon chain may optionally be interrupted by one of the following groups:

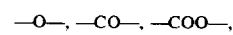

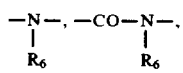

in which $R_6$ is a hydrogen atom, or a straight or branched alkyl radical having from 1 to 4 carbon atoms, and/or may bear one of the substituents:

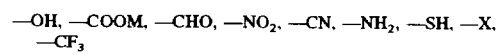

wherein X is a halogen atom.

15. The process as defined by claim 14, wherein Q is a straight or branched, saturated or unsaturated, acyclic aliphatic hydrocarbon radical optionally bearing a cyclic substituent, with the proviso that said acyclic aliphatic hydrocarbon radical may be bonded to a ring member via a simple valence bond or by one of the following groups:

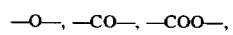

$$-\underset{\underset{R_6}{|}}{N}-, -CO-\underset{\underset{R_6}{|}}{N}-,$$

$$-S-, -SO_2-$$

in which $R_6$ is a hydrogen atom, or a straight or branched alkyl radical having from 1 to 4 carbon atoms.

16. The process as defined by claim 3, wherein formula (I), Q is a saturated or unsaturated, mono- or polycyclic heterocyclic radical having up to two heteroatoms per heterocycle, with the proviso that the carbon atoms of the heterocycles may optionally be substituted by a substituent R, in which R is a straight or branched alkyl radical having from 1 to 6 carbon atoms, a straight or branched alkenyl radical having from 2 to 6 carbon atoms, a straight or branched alkoxy radical having from 1 to 6 carbon atoms, or one of the radicals —$R_2OH$, —$R_2$—COOM, —$R_2$—CHO, —$R_2$—$NO_2$, —$R_2$—CN, —$R_2$—$NH_2$, —$R_2$—SH, —$R_2$—X or —$R_2$—$CF_3$, in which $R_2$ is a simple valence bond, or a saturated or unsaturated, straight or branched divalent hydrocarbon radical having from 1 to 4 carbon atoms; and X is a halogen atom.

17. The process as defined by claim 3, said carboxylic acid salt of formula (I) comprising a salt of a saturated aliphatic monocarboxylic or dicarboxylic acid, an unsaturated aliphatic monocarboxylic or dicarboxylic acid, a saturated or unsaturated carbocyclic carboxylic acid, a heterocyclic carboxylic acid, an aromatic carbocyclic carboxylic acid, a saturated or unsaturated arylaliphatic carboxylic acid, a halogenated carboxylic acid, an aliphatic, cycloaliphatic or arylaliphatic hydroxycarboxylic acid, an alkoxy or phenoxycarboxylic acid, an oxocarboxylic acid, an acyloxycarboxylic acid, an amidocarboxylic acid, or of an N-protected aminocarboxylic acid.

18. The process as defined by claim 17, said carboxylic acid salt of formula (I) comprising a salt of salicyclic or 4-hydroxysalicylic acid, of acetic or propionic acid or of hydroxy, halo, aryl, or aryloxy derivative thereof, of benzoic acid or of lower alkyl, acetoxy or acetamido derivative thereof, of nicotinic acid, or of an N-protected aminocarboxylic acid.

19. The process as defined by claim 1, said organic halocompound having the formula (III):

$$R_7-X \qquad (III)$$

in which X is a halogen atom situated other than in a vinyl or alkynyl position and $R_7$ is an optionally substituted straight or branched, saturated or unsaturated, acyclic aliphatic radical, a monocyclic or polycyclic, saturated or unsaturated, cycloaliphatic radical, or a straight or branched, saturated or unsaturated aliphatic radical bearing a cyclic substituent.

20. The process as defined by claim 19, wherein formula (III), $R_7$ is a straight or branched alkyl, alkenyl, alkadienyl or alkynyl radical, with the proviso that the hydrocarbon chain may optionally be interrupted by one of the following groups:

$$-O-, -CO-, -COO-,$$

$$-\underset{\underset{R_8}{|}}{N}-, -CO-\underset{\underset{R_8}{|}}{N}-$$

in which $R_8$ is a hydrogen atom or an alkyl radical having from 1 to 4 carbon atoms, or a cyclohexyl or phenyl radical, and/or may be substituted by one of the following Y substituents: an —OH group, a —COOH group, a —CHO group, and —$NO_2$ group, a —C≡N group, a non-quaternizable or N-protected amino group, a halogen atom, or a —$CF_3$ group.

21. The process as defined by claim 19, wherein formula (III), $R_7$ is a cycloalkyl or cycloalkenyl radical, optionally substituted by one or more of the following Y substituents: an —OH group, a —COOH group, a —CHO group, an —$NO_2$ group, a —C≡N group, a non-quaternizable or N-protected amino group, a halogen atom, or straight —$CF_3$ group, and/or by one or more straight or branched alkyl or alkoxy radicals having from 1 to 4 carbon atoms, or radicals of the formulae:

$$R_8-CO-, R_8-COO-, R_8-O-CO-,$$

$$R_8-\underset{\underset{R_8}{|}}{N}-, R_8-CO-\underset{\underset{R_8}{|}}{N}-, R_8-\underset{\underset{R_8}{|}}{N}-CO-$$

in which $R_8$ is a hydrogen atom, an alkyl radical having from 1 to 4 carbon atoms, or a cyclohexyl or phenyl radical.

22. The process as defined by claim 19, wherein formula (III), $R_7$ is a straight or branched, saturated or unsaturated, acyclic aliphatic radical bearing a cyclic substituent, said acyclic aliphatic radical optionally being bonded to a ring member via a simple valence bond or by one of the following groups:

$$-O-, -CO-, -COO-,$$

$$-\underset{\underset{R_8}{|}}{N}-, -CO-\underset{\underset{R_8}{|}}{N}-$$

in which $R_8$ is a hydrogen atom, an alkyl radical having from 1 to 4 carbon atoms, or a cyclohexyl or phenyl radical.

23. The process as defined by claim 19, wherein formula (III), $R_7$ is a straight or branched alkyl radical having from 1 to 8 carbon atoms, a straight or branched alkenyl radical having from 2 to 8 carbon atoms and comprising an ethylenic double bond in the beta position to the halogen atom X a cyclohexyl radical optionally substituted by a straight or branched alkyl radical having from 1 to 4 carbon atoms, or an arylalkyl radical having the formula:

$$\text{+CH}_2\text{+}_m\text{-}\phantom{x}\bigcirc$$

in which m is an integer ranging from 1 to 4.

24. The process as defined by claim 19, said organic halocompound comprising allyl bromide, allyl chloride benzyl bromide, benzyl chloride, isopropyl bromide, croty chloride, 1-chloro-2-butene or cyclohexyl bromide.

25. The process as defined by claim 1, said phase transfe catalyst comprising an onium salt.

26. The process as defined by claim 25, the onium ion o said salt having one of the following formulae:

$$\underset{R_{10}}{\overset{R_9}{\diagdown}}\overset{\oplus}{W}\underset{R_{12}}{\overset{R_{11}}{\diagup}} \qquad (IV)$$

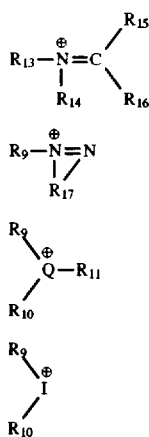

wherein W is N, P or As; Q is S, O, Se, S=O or C; $R_9$, $R_{10}$, $R_{11}$ and $R_{12}$, which may be the same or different, are each a straight or branched alkyl radical having from 1 to 16 carbon atoms, optionally substituted by one or more phenyl, hydroxyl, halogen, nitro, alkoxy or alkoxycarbonyl radicals or atoms, the alkoxy radicals having from 1 to 4 carbon atoms, a straight or branched alkenyl radical having from 2 to 12 carbon atoms, an aryl radical having from 6 to 10 carbon atoms, optionally substituted by one or more alkyl radicals having from 1 to 4 carbon atoms, an alkoxy or alkoxycarbonyl radical, the alkoxy radical having from 1 to 4 carbon atoms, or a halogen atom, with the proviso that two of the radicals $R_9$ to $R_{12}$ may together form a straight or branched alkylene, alkenylene or alkadienylene radical having from 3 to 6 carbon atoms; $R_{13}$, $R_{14}$, $R_{15}$, and $R_{16}$, which may be the same or different, are each a straight or branched alkyl radical having from 1 to 4 carbon atoms, with the proviso that the radicals $R_{15}$ and $R_{16}$ may together form an alkylene radical having from 3 to 6 carbon atoms and the radicals $R_{14}$ and $R_{15}$ or $R_{15}$ and $R_{16}$ may together form an alkylene, alkenylene or alkadienylene radical having 4 carbon atoms and constituting a nitrogen heterocycle with the nitrogen atom from which they depend; and $R_{17}$ is a divalent radical which, together with the two nitrogen atoms from which it depends, constitutes an optionally substituted ring of 4 to 6 atoms which may include one or more nitrogen, sulfur and/or oxygen bridging atoms.

27. The process as defined by claim 26, the anion of said onium salt comprising $SnCl_6^-$, $SbCl_6^-$, $B(Ph)_4^-$, $PO_4^{3-}$, $HPO_4^{2-}$, $H_2PO_4^-$, $CH_3SO_3^-$, $Ph\text{—}SO_3^-$, $HSO_4^-$, $NO_3^-$, $SO_4^{2-}$, $Cl^-$, $Br^-$, $I^-$ or $OH^-$, wherein Ph is phenyl.

28. The process as defined by claim 26, the onium ion of said salt comprising a quaternary ammonium ion, a quaternary phosphonium ion, a sulfonium ion, or an iodonium ion.

29. The process as defined by claim 1, said phase transfer catalyst comprising tributylbenzylammonium or phosphonium chloride or bromide, tetramethylammonium or phosphonium chloride or bromide, tetraethylammonium or phosphonium chloride or bromide, or tetrabutylammonium or phosphonium chloride or bromide.

30. The process as defined by claim 1, wherein the molar ratio of the number of carboxylate functions comprising said carboxylic acid salt to the number of reactive halogen atoms comprising said organic halocompound ranges from 0.5 to 2.0:1.0.

31. The process as defined by claim 1, wherein the molar ratio of said phase transfer catalyst to said phase transfer catalyst to said carboxylic acid salt ranges from 0.01 to 0.50:1.0.

32. The process as defined by claim 1, comprising gradually introducing said carboxylic acid salt into reaction admixture of said organic halocompound and said phase transfer catalyst.

33. The process as defined by claim 1 wherein the organic phase is separated from the aqueous phase.

34. The process as defined by claim 1, wherein said aqueous reaction medium has a water concentration ranging from 500 to 100% by weight.

* * * * *